United States Patent [19]

Pan et al.

[11] Patent Number: 4,460,385
[45] Date of Patent: Jul. 17, 1984

[54] PROCESS FOR THE REMOVAL OF ACID GASES FROM HYDROCARBON GASES CONTAINING THE SAME

[75] Inventors: Yen-Chi Pan, Westfield; Eugene L. Stogryn, Edison, both of N.J.

[73] Assignee: Exxon Research and Engineering Co., Florham Park, N.J.

[21] Appl. No.: 444,856

[22] Filed: Nov. 26, 1982

[51] Int. Cl.³ .............................................. B01D 53/14
[52] U.S. Cl. ............................................. 55/73; 55/68
[58] Field of Search ...................... 55/68, 73; 548/565

[56] References Cited

U.S. PATENT DOCUMENTS

| | | | |
|---|---|---|---|
| 2,385,704 | 9/1945 | Hooker et al. | 55/73 |
| 2,649,166 | 8/1953 | Porter et al. | 55/19 |
| 2,863,527 | 12/1958 | Herbert et al. | 55/68 X |
| 2,926,751 | 3/1960 | Kohl et al. | 55/68 X |
| 3,161,461 | 12/1964 | Deal, Jr. et al. | 55/73 X |
| 3,266,219 | 8/1966 | Woertz | 55/73 X |
| 3,324,627 | 6/1967 | Kohrt | 55/32 |
| 3,347,621 | 10/1967 | Papadopoulos et al. | 55/73 X |
| 3,632,519 | 1/1972 | Gustafson | 55/68 X |
| 3,653,809 | 4/1972 | Wehner et al. | 55/73 X |
| 3,656,275 | 4/1972 | Hunter | 55/73 X |
| 3,733,779 | 5/1973 | Bellisio et al. | 55/73 |
| 3,733,780 | 5/1973 | Bellisio et al. | 55/73 |
| 3,733,781 | 5/1973 | Bellisio et al. | 55/73 |
| 3,738,086 | 6/1973 | Bellisio et al. | 55/73 X |
| 3,773,896 | 11/1973 | Preusser et al. | 55/73 X |
| 3,966,875 | 6/1976 | Bratzler et al. | 55/73 X |
| 4,080,424 | 3/1978 | Miller et al. | 55/73 X |
| 4,345,918 | 8/1982 | Meissner | 55/73 X |

OTHER PUBLICATIONS

G. Hochgesand, "Rectisol and Purisol", *Industrial and Engineering Chemistry*, vol. 62, (1970) pp. 37–43.
"Fluor Solvent", *Hydrocarbon Processing*, Apr. 1979, pp. 112, 117–119.

Primary Examiner—Robert H. Spitzer
Attorney, Agent, or Firm—Albert P. Halluin; Henry E. Naylor

[57] ABSTRACT

Disclosed is a process for selectively removing one or more acid gases from hydrocarbon feed streams containing the same using hydroxyalkyl pyrrolidones as a physical solvent for each of the acid gases or aqueous mixtures containing the physical solvent. The process may be operated using the generalized flow sheet of a typical industrial acid gas treating plant as shown in FIG. 1.

9 Claims, 1 Drawing Figure

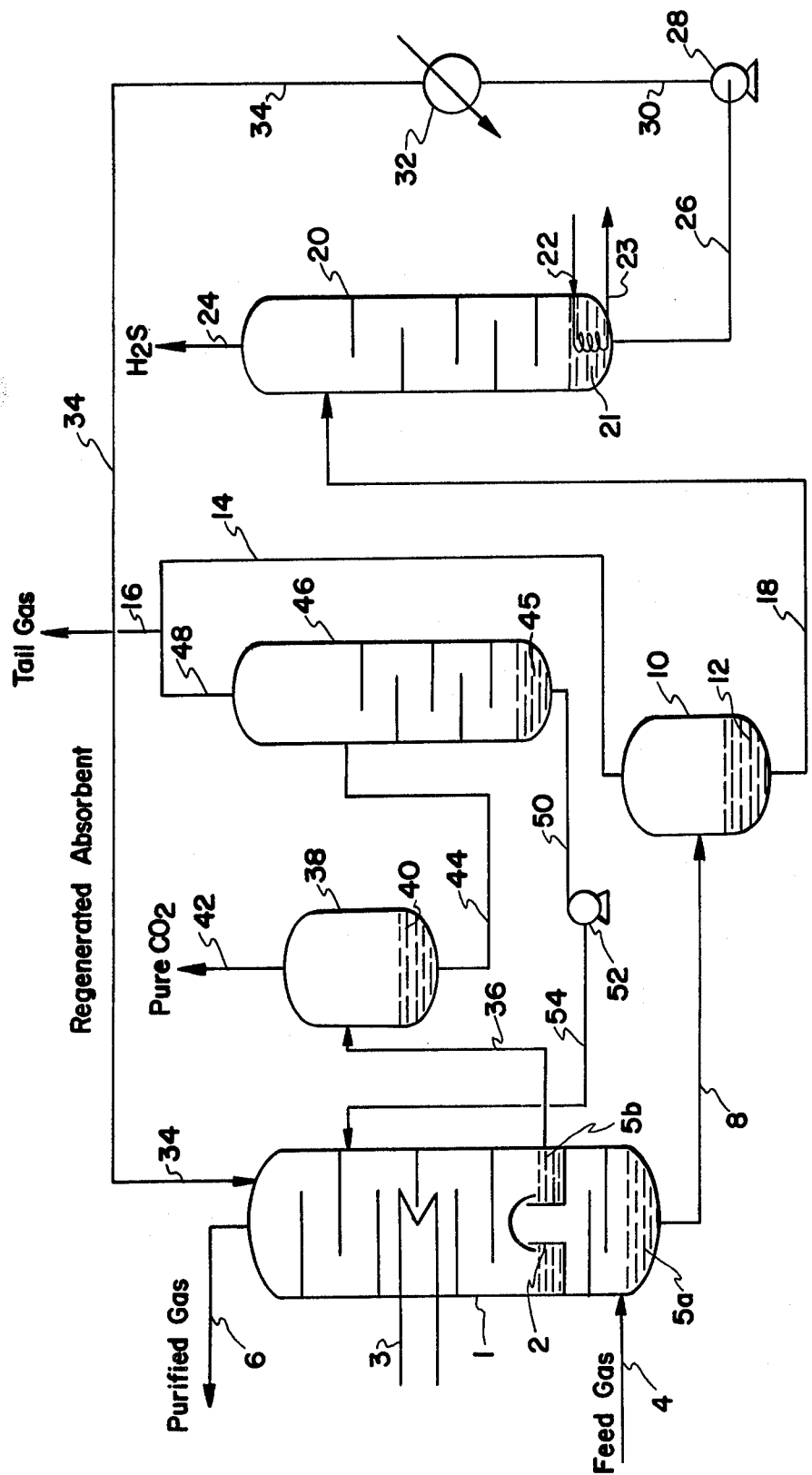

PROCESS FOR THE REMOVAL OF ACID GASES FROM HYDROCARBON GASES CONTAINING THE SAME

The present invention relates to a process for removing by absorption acid gases from gaseous mixtures containing the same by scrubbing under pressure with a solvent.

High pressure industrial gases such as natural gases, synthesis gases and refinery gases containing hydrocarbons, CO and $H_2$ often contain undesirable acid gas compounds such as $CO_2$, $H_2S$, COS, $CS_2$, mercaptans, sulfides, disulfides and the like. Removal of some of these acid gas compounds may be readily accomplished by scrubbing with amine solutions. However, to eliminate sulphur impurities other than $H_2S$, it is often necessary to employ additional purification procedures.

These additional procedures typically involve the use of solvents known as "physical solvents." These physical solvents, in contrast with amine absorbents, do not chemically combine with the acid gas compounds. Many of the known physical solvents are capable of simultaneously absorbing all the undesirable acid gas compounds in one scrubbing operation. Thus, physical solvents have been used for selective removal of acid gases from non-acidic compounds containing acid gases by solubilizing the gases through partial pressure effect of the acid gas compounds.

Physical solvents are receiving greater considerations for high pressure acid gas treating processes due to the following reasons:
 (a) physical solvents may be regenerated by stepwise depressurizing without heat consumption (Due to the rising cost of energy, this energy-saving solvent regeneration step becomes a significant advantage over the other processes); and
 (b) the solubilities of the acid gases in the physical solvents are proportional to the partial pressure of the gases. (Due to the current trend for manufacturing under higher gas pressures, the loading of the acid gas increases and, therefore, the requirement for solvent circulation is reduced).

Physical solvents in commercial use today include the dimethylether of polyethylene glycol (e.g., utilizing a process such as disclosed in U.S. Pat. No. 2,649,166), N-methyl pyrrolidone (e.g., utilizing a process such as disclosed in U.S. Pat. No. 3,324,627), methanol (e.g., utilizing a process such as disclosed in U.S. Pat. No. 2,863,527) and propylene carbonate (e.g., utilizing a process such as disclosed in U.S. Pat. No. 2,926,751). A brief description of these physical solvent processes can be found in Hydrocarbon Processing, pages 112, 117–119 (April, 1979) and Ind. Eng. Chem., 62 (7) 37–43 (1970). These physical solvents, while useful in their own right, have the disadvantage of solubilizing hydrocarbons. Hydrocarbon solubility is the largest drawback for the physical solvents in commercial use today. Thus, a physical solvent with the highest ratio of acid gas/hydrocarbon solubility will reduce the product loss during the acid gas removal.

It has now been discovered that certain hydroxyalkyl heterocyclic compounds exhibit a relatively high ratio of acid gas/hydrocarbon solubility. This higher selectivity is due principally to a reduction in hydrocarbon solubility. The apparent reason for the lower hydrocarbon solubility of these physical solvents is due to the more polar nature of the hydroxyalkyl heterocyclic compound. Thus, the physical solvents of the invention significantly reduce the hydrocarbon product loss and the higher boiling point of these compounds results in reduction of solvent loss during use in the acid gas removal process.

SUMMARY OF THE INVENTION

As one embodiment of the invention there is provided a process for the selective removal of acid gases from a hydrocarbon-containing gas stream containing the same, wherein at least one of the acid gases present has a partial pressure of at least about one bar. The process comprises, in an absorption step, contacting the gas stream with a physical solvent comprising at least one hydroxylalkyl pyrrolidone or an aqueous mixture containing the physical solvent so as to absorb at least a portion of the acid gases and, in a desorption step, removing at least a portion of said acid gases from the physical solvent.

Typical hydroxyalkyl pyrrolidones include, e.g., N-hydroxylethyl-2-pyrrolidone, N-(3-hydroxylpropyl)-2-pyrrolidone, N-(2-hydroxylpropyl)-2-pyrrolidone and mixtures thereof. The physical solvent may comprise an aqueous mixture including up to 20% by weight water, preferably 5 to about 15% by weight water.

Another embodiment of the invention pertains to treating industrial gases or raw natural gases containing $CO_2$ and/or $H_2S$ and at least one of the compounds selected from the group consisting of COS, $CS_2$, mercaptans, sulfides, and disulfides with at least one hydroxyalkyl pyrrolidone. The industrial gases to be treated may contain hydrocarbon gases (e.g., methane, ethane, propane, and butane, and $C_4^+$ compounds), hydrogen, carbon monoxide, nitrogen, steam and their mixtures.

BRIEF DESCRIPTION OF THE DRAWING

FIG. 1 is a flow sheet of a typical industrial acid gas treating plant for which the present invention may be practiced.

DESCRIPTION OF THE PREFERRED EMBODIMENTS

The process of the invention comprises selectively removing from a gaseous stream acid gases such as $CO_2$ and/or $H_2S$, at least one of which has a partial pressure of at least one bar, and at least one compound selected from the group consisting of hydrocarbons, hydrogen and carbon monoxide. The gaseous stream may also contain COS, $CS_2$, mercaptans, sulfides or disulfides, nitrogen or water vapor. The hydroxyalkyl pyrrolidone may be used in substantially pure form or in admixture with up to 20% by weight water, preferably 5 to about 15% by weight water.

In a typical processing operation, absorption is carried out at a total pressure greater than atmospheric, e.g., 10 to 100, preferably 30 to 80 bars, and at a temperature ranging from 0° to about 50° C., preferably ranging from about 20° to about 40° C. The rich solvent is essentially regenerated by at least one and preferably two successive expansion or flash operation steps. In a typical two-step expansion, the mixture obtained in the first expansion or flash step may be recycled in the absorber. The solvent may be reheated and stripped with an inert gas (e.g., a purified gas), or with steam.

The advantages of using hydroxyalkyl pyrrolidones as physical solvents in the practice of the instantly claimed invention are shown in Table I, which indicates the solubilities of $H_2S$, $C_3H_8$ and $CO_2$, the selectivity values for $H_2S/C_3H_8$, $CO_2/C_3H_8$ and $H_2S/CO_2$ and the boiling points for N-hydroxyethyl-2-pyrrolidone (NHP) compared against N-methyl pyrrolidone, (NMP), propylene carbonate, a dimethylether of polyethylene glycol and methanol. These tests were conducted at 25° C. and up to 6.8 bar pressure.

TABLE 1

SOLUBILITIES AND SELECTIVITIES FOR PHYSICAL SOLVENTS

| Solvent | Solubility at 25° C. (cc.(g)/cc.(l)/Atm.) | | | Selectivity | | | B.P. (°C.) |
|---|---|---|---|---|---|---|---|
| | $H_2S$ | $C_3H_8$ | $CO_2$ | $H_2S/C_3H_8$ | $CO_2/C_3H_8$ | $H_2S/CO_2$ | |
| NHP[1] | 29.2 | 1.29 | 3.87 | 22.6 | 3.0 | 7.5 | 295 |
| NMP[2] | 39.8 | 3.95 | 3.4 | 10.1 | 0.86 | 11.7 | 202 |
| Propylene Carbonate | 13.2 | 2.6 | 3.7 | 3.8 | 1.42 | 3.6 | 240 |
| DMETEG[3] | 26.0 | 4.65 | 3.6 | 5.6 | 0.77 | 7.2 | 276 |
| Methanol | 15 | 6.8 | 3.5 | 2.2 | 0.51 | 4.3 | 64.7 |

[1] N—hydroxyethyl-2-pyrrolidone (NHP)
[2] N—methyl pyrrolidone (NMP)
[3] Dimethylether of tetraethylene glycol (DMETEG)

These data show that NHP of the present invention has the lowest solubility for the hydrocarbon propane, and the highest selectivities for $H_2S$ and $CO_2$ over propane ($C_3H_8$). This advantage, coupled with its relatively high boiling point of 295° C., makes it an excellent physical solvent for selectively removing acid gases such as $CO_2$ from hydrocarbon gases. Similar advantages are anticipated for related hydroxyalkyl pyrrolidones of the invention.

Referring to FIG. 1, generally, there is shown absorption column 1, fitted with bubble cap means 2 and intermediate cooling means 3. Contaminated feed gas containing $H_2S$ and $CO_2$ enters the absorption column 1 via pipe 4 at a pressure of 10 and 100 bars where it comes into contact with a liquid physical solvent absorbent solution at a temperature ranging from 0° to 50° C., which may consist of N-hydroxyethyl-2-ppyrrolidone. The absorption column consists of two stages, or a lower and upper portion. The lower portion, 5a, is primarily for $H_2S$ removal and the upper portion, 5b, is for $CO_2$ removal. Purified gas is emitted from the absorber via pipe 6. The $H_2S$- and $CO_2$-enriched absorbent solution is taken from absorption column 1 via pipe 8 to intermediate flash drum 10. The absorbed $CO_2$ in the saturated absorbent 12 is flashed out of the drum via pipes 14 and 16 as tail gas. As a result, the $H_2S$ concentration in the absorbent solution is enriched relative to $CO_2$. The absorbent solution enriched with $H_2S$ is transported to regenerator 20 via pipe 18 wherein the $H_2S$ is removed from the absorbent solution via pipe 24 (e.g., to a Claus plant) by action of steam regeneration via steam injection from pipe 22 and removal of same via pipe 23. The regenerated absorbent 21 is removed from regenerator 20 and returned to absorber 1 via pipes 26, 30 and 34 whereby the recirculation is aided by compressor 28 and the heat is removed before return to the absorption column via heat exchanger 32.

In the event pure $CO_2$ is desired, $CO_2$-enriched absorbent 5b is taken from the upper portion of the absorber 1 and transferred to a median pressure desorption drum 38 via pipe 36. The $CO_2$-enriched absorbent solution 40 is freed of $CO_2$ which is then emitted from the desorption drum 38 via pipe 42. The regenerated absorbent solution 40 is transported from desorption drum 38 via pipe 44 to a low pressure desorption drum 46 where further regeneration of the absorption solution takes place. The $CO_2$ rich gas is vented as tail gas via pipes 48 and 16. The regenerated absorption solution 45 is recirculated to absorber 1 via pipes 50 and 54 by aid of compressor 52.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A process for the selective removal of one or more acid gases from a hydrocarbon-containing gas stream, containing the same, wherein at least one of the acid gases present has a partial pressure of at least about one bar, said process comprising, in an absorption step, contacting said gas stream with a solvent for the gases or aqueous mixture containing said solvent, and, in a desorption step, removing at least a portion of said acid gases from said solvent, said solvent comprising at least one hydroxyalkyl pyrrolidone.

2. The process of claim 1 wherein said acid gas are selected from the group consisting $CO_2$, $H_2S$, COS, $CS_2$, mercaptans, sulfides, disulfides and mixtures thereof.

3. The process of claim 1 wherein said hydrocarbon contained in said gas stream is selected from methane, ethane, propane, butane or mixtures thereof.

4. The process of claim 3 wherein said gas stream is a raw natural gas.

5. The process of claim 1 wherein said absorption step is carried out at a pressure of at least atmospheric pressure and at a temperature ranging from about 0° C. to about 50° C.

6. The process of claim 1 wherein said aqueous mixture contains up to 20% by weight water.

7. The process of claim 1 wherein said aqueous mixture contains from about 5 to about 15% by weight water.

8. The process of claim 1 wherein said solvent is selected from the group consisting of N-(2-hydroxyethyl)-2-pyrrolidone, N-(3-hydroxypropyl)-2-pyrrolidone, N-(2-hydroxypropyl)-2-pyrrolidone and mixtures thereof.

9. The process of claim 8 wherein said solvent is N-(2-hydroxyethyl)-2-pyrrolidone.

* * * * *